(12) United States Patent  (10) Patent No.: US 7,762,970 B2
Henderson et al.  (45) Date of Patent: Jul. 27, 2010

(54) ORTHOPAEDIC CAST WITH OUTRIGGER ATTACHMENT

(76) Inventors: Wendy Henderson, 475 Escondido Ct., Camarillo, CA (US) 93010; Tracy Grim, 5600 Lakeview Canyon Rd., Thousand Oaks, CA (US) 91362; Joe Iglesias, 1930 Brush Oak St., Newbury Park, CA (US) 91320

( * ) Notice: Subject to any disclaimer, the term of this patent is extended or adjusted under 35 U.S.C. 154(b) by 154 days.

(21) Appl. No.: 11/902,680

(22) Filed: Sep. 25, 2007

(65) Prior Publication Data

US 2008/0091130 A1   Apr. 17, 2008

Related U.S. Application Data

(60) Provisional application No. 60/847,101, filed on Sep. 26, 2006.

(51) Int. Cl.
  A61F 5/00 (2006.01)
  A61F 13/06 (2006.01)
  A61F 5/37 (2006.01)
(52) U.S. Cl. .................. 602/8; 602/21; 602/63; 128/880; 128/878
(58) Field of Classification Search .......... 602/1, 602/8, 7, 14, 18, 19, 62, 5, 6, 21–23, 61–63; 128/880, 877, 878; 2/16
See application file for complete search history.

(56) References Cited

U.S. PATENT DOCUMENTS

| 1,471,948 | A |  | 10/1923 | Cox et al. |
| 4,294,240 | A |  | 10/1981 | Thill |
| 4,382,439 | A |  | 5/1983 | Shen |
| 4,524,464 | A |  | 6/1985 | Primiano et al. |
| 4,768,502 | A |  | 9/1988 | Lee |
| 4,852,556 | A | * | 8/1989 | Groiso ................ 602/5 |
| 4,928,678 | A |  | 5/1990 | Grim |
| 4,996,979 | A |  | 3/1991 | Grim et al. |
| 5,356,371 | A |  | 10/1994 | Hubbard |
| 5,807,293 | A |  | 9/1998 | Wedge, Jr. |
| 5,928,172 | A |  | 7/1999 | Gaylord |
| 6,039,706 | A |  | 3/2000 | Bolla et al. |
| 6,139,513 | A |  | 10/2000 | Grim et al. |
| 6,186,966 | B1 |  | 2/2001 | Grim et al. |
| 6,461,317 | B1 |  | 10/2002 | Grim et al. |
| 6,482,167 | B2 |  | 11/2002 | Grim et al. |
| 6,824,522 | B2 |  | 11/2004 | Henderson et al. |
| 6,929,613 | B2 |  | 8/2005 | Henderson et al. |
| 7,018,351 | B1 |  | 3/2006 | Iglesias et al. |
| 2004/0210177 | A1 | * | 10/2004 | Grim et al. ........... 602/8 |
| 2005/0043664 | A1 | * | 2/2005 | Reaux ................ 602/63 |
| 2005/0234374 | A1 |  | 10/2005 | Grim et al. |
| 2005/0234375 | A1 |  | 10/2005 | Grim et al. |
| 2006/0155226 | A1 |  | 7/2006 | Grim et al. |

* cited by examiner

*Primary Examiner*—Patricia M Bianco
*Assistant Examiner*—Ophelia Hawthorne
(74) *Attorney, Agent, or Firm*—Bacon & Thomas, PLLC

(57) ABSTRACT

A cast for use in limiting movement of the hand to promote healing of an injured body part includes a water hardenable orthopaedic blank for mounting on the forearm, preferably with a thumb hole, and an outrigger, also impregnated with water hardenable material, secured to the blank for holding the thumb or fingers against movement. This construction minimizes irritation of the web between the thumb and forefinger and reduces discomfort and trauma caused by chafing and pressure.

19 Claims, 6 Drawing Sheets

FIG. 3
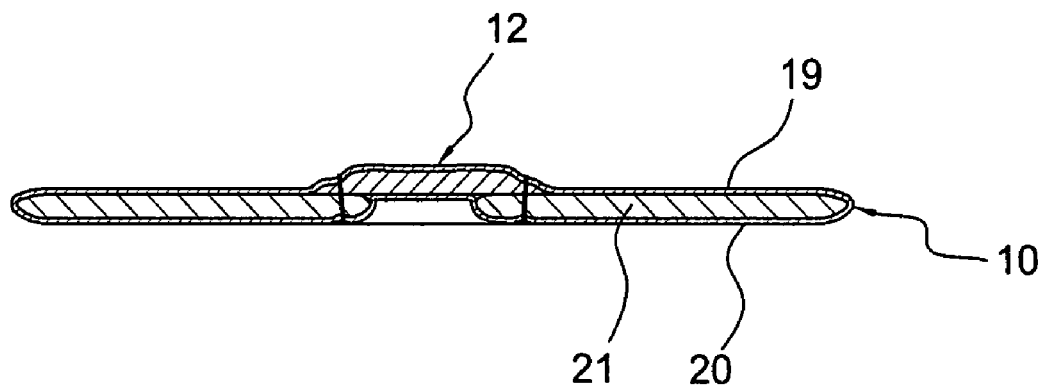
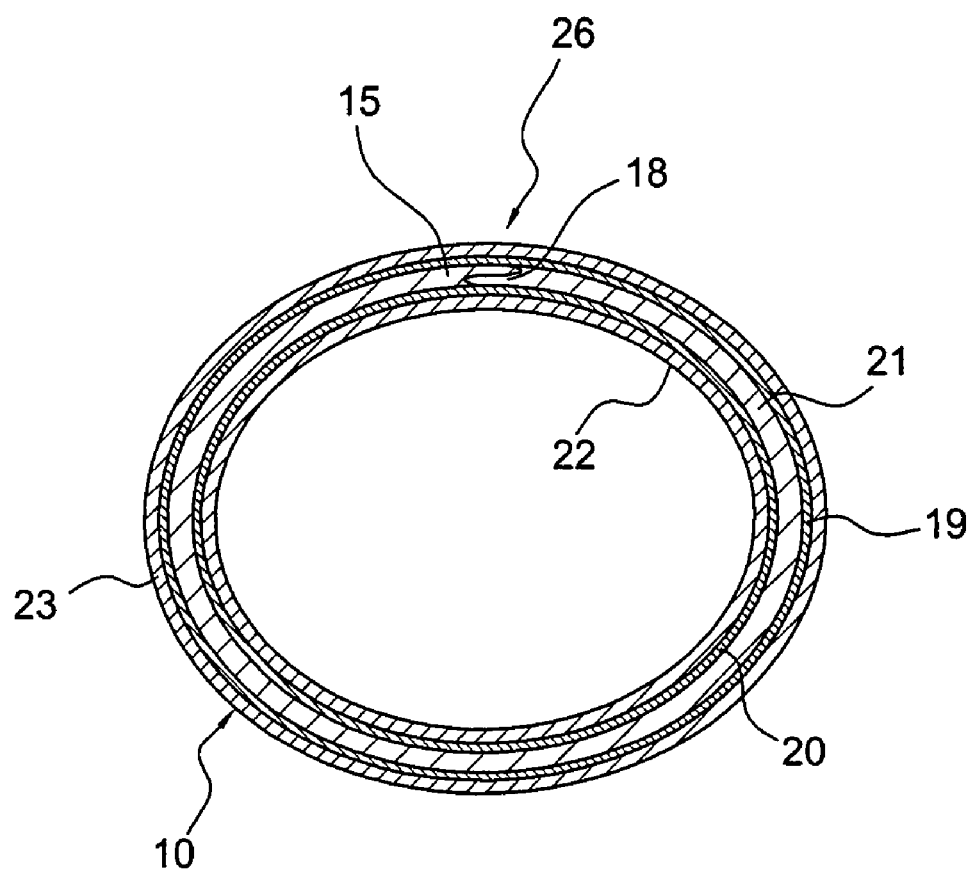
FIG. 5

ORTHOPAEDIC CAST WITH OUTRIGGER ATTACHMENT

CROSS REFERENCE TO RELATED APPLICATIONS

This application claims the benefit of priority of U.S. Provisional Patent Application No. 60/847,101, filed on Sep. 26, 2006.

BACKGROUND

This invention relates to a cast useful for orthopaedic devices, particularly a cast for the forearm and the thumb or fingers of a patient. More generally, the invention relates to providing a cast configuration for use with extended portions of the anatomy.

Treatment of injuries such as bone fractures, involved immobilization of portions of the body for a period of time. Such immobilization can be provided by different cast materials, for example, fabrics impregnated with water hardenable material such as urethane or Plaster of Paris. Since casts remain on the body for a long time, this often causes considerable discomfort and trauma to the patient. Chafing and pressure may result in ulceration of the skin underlying the cast.

With regard to casts for injuries of the thumb, these have often been handled theretofore by using casting tape and wrapping the casting tape around the forearm and the thumb. However, the tape is usually wrapped through the area between the thumb and the forefinger and, upon hardening, the hardened cast tape may cause chafing and irritation in this web area unless great care is taken. The comfort of each cast is dependent upon the technique and experience of the person applying the cast.

It is also desirable to provide an effective material to provide a cushion between the cast and the body. This, however, does not always effectively address the comfort issue.

SUMMARY

The exemplary embodiments of this invention are directed to providing a cast configuration with improved comfort to areas of the body, such as the area between the thumb and the forefinger which would otherwise be unduly uncomfortable. The embodiments also provide better function and an easier application than a traditional cast.

According to one illustrative embodiment, there is provided a cast for the forearm and thumb for use to promote healing of an injury. There is a first material provided with a thumb hole to form a rigid member to limit movement of at least the wrist area of the injured bodily part. There is a second material attached to the first material by any means, which forms a rigid member for location about the thumb, namely a thumb spica. By limiting the amount of material and eliminating the need for skilled technique, this design effectively avoids discomfort to the area adjacent to a web portion of the hand between the thumb and index finger. Also, the use of the second material, which is, in part, relatively separate from the first material, limits irritation and trauma to the periphery of the web and to the portions distal to the periphery.

In practice, a first material or blank is provided with a hole for the thumb to extend through the first material from one side to the other. There is also the second material, a thumb spica, which may be secured to one side of the first material. Both the blank and the associated thumb spica may be impregnated with water-hardenable material, and are activated by dipping into water. After the thumb is pushed through the hole, the second material, the thumb spica, wraps around the thumb. The first material is wrapped around the hand, wrist and forearm. This first material can be either completely circumferential or may only extend partially around the forearm. In this process, the thumbhole may be configured to be fairly loose in its spacing around the thumb to avoid tight engagement with the web between the thumb and forefinger.

Padding material may also be provided as a liner between the cast and the skin. It is a soft and flexible material that provides comfort to the sensitive area of the body.

The first and second materials are suitably treated to cause rigidity, as noted above. Further arrangements may be provided for wrapping around the first and/or second materials to provide reinforcement, enhance rigidity, or merely to properly secure and mold the materials to the body.

The water-hardenable material may be a double knit-type fabric (also referenced herein as "spacer" material) with an inner woven or knit layer, an outer woven or knit material layer and filaments extending between and spacing the two layers apart, with the filaments being integrally woven into the inner and outer layers. The two layers of fabric, as well as the space between the two layers, may be impregnated with water-hardenable urethane.

It is further noted that the thumbhole in the blank has a curved configuration and the thumb spica is curved where it is secured to the blank adjacent the thumbhole. Accordingly, with the thumb spica being curved, the assembly has increased structural strength comparable to a structural beam, as compared to the strength of a flat member of the same material.

More generally, the invention contemplates the use of a basic blank, preferably configured to encompass a principal portion of the anatomy of the patient, and an outrigger or attachable piece which may be permanently or removably secured to the blank for restraining movement of an extended injured portion of the anatomy. In addition to the thumb spica, the invention is applicable to ulnar gutters or radial gutters, for specific additional examples. In this regard, the two principal bones of the forearm are the radius and the ulna, with the radius being the inner forearm bone and the ulna being the outer forearm bone. An ulnar gutter is a cast which immobilizes the fourth and fifth fingers of the hand (generally aligned with the ulna), while a radial gutter cast immobilizes the forefinger and, when needed, the adjacent finger or fingers of the hand.

Concerning materials to be used, the preferred material is fiberglass double-knit, or spacer material. Other materials which may be used include spacer material using various fibers, foam, foam laminates and other known casting materials.

If a spacer or foam laminate is used, it is useful to knock down the edges of the blank by thermoforming prior to coating. This can be done in certain areas to reduce the profile or in the areas of overlap to eliminate any steps in the underside of the cast or splint. Pressed edges cause a reduction in the strength of the material and therefore create a "flex-edge" feature reducing or eliminating any stiff edges which might otherwise irritate the skin. Using spacer or double-knit material, it is also possible to create the thinned sections during knitting, eliminating the need for thermoforming, yet yielding the same benefits.

The outrigger attachment can be attached, either permanently or made removable. For permanent fixation, the attachment can be applied prior to coating using one of several methods: adhesive, sewing, ultrasonic sewing, riveting, or the like. It can also be supplied as a separate piece which is wrapped around the anatomy after the blank has already been applied and adhered to the blank by lamination of the resin in the blank and the attachment. For a removable outrigger attachment, the blank and the attachment pieces can be cured separately and then joined together, for example by hook and loop-type material, sold under the trademark Velcro®, making the attachment removably affixed.

There are three principal products which use the outrigger attachment concept, the first being a thumb spica cast or splint. The blank for this design is one that fits the forearm and has a thumbhole with a pre-made web space. This pre-made web space is narrow, increasing the comfort for the wearer and eliminating any especially skilled technique required to immobilize this complex and sensitive area of the anatomy with traditional casting materials. A second piece for immobilizing the thumb is attached either permanently or removably around the thumbhole in the blank. When in use, the blank is applied by placing the injured thumb through the thumb hole, wrapping the blank around the forearm, and wrapping the attached thumb piece around the thumb, with the blank and attached piece being dipped in water prior to application.

The second and third products using outrigger attachments are very similar to each other in that a blank is used on either the ulnar or radial side of the hand and shaped to fit the anatomy of the hand and forearm. It is preferable but not necessary for these blanks to include thumbholes similar to the thumb spica blank. In both cases, the outrigger piece can be attached to the blank by any of the arrangements described previously. For the ulnar gutter cast/splint, the attachment is used to wrap and immobilize the fourth and fifth fingers. In the case of the radial cast/splint, the attachment is used to wrap and immobilize the first finger and, in some cases, the adjacent finger.

In accordance with another aspect of the invention, an orthopaedic cast with an outrigger includes a main blank formed of fabric or material impregnated with water hardenable material and specially formed in an irregular configuration to fit a portion of the anatomy; and an outrigger also impregnated with hardenable material extending forward from the main blank and including sideward extending flaps to extend around one or more of the extremities such as the finger or fingers or the thumb of a patient.

There are many benefits of this type of outrigger cast arrangement. First is a quicker cast application because it consists of only one layer of material. The construction of the double-knit material also allows for better conformability and eliminates wrinkling or irregularities in the underside cast surface. There is also a premade web space which is a further time-saver and increases the comfort of the final product.

Other objects, features and advantages will become apparent from a consideration of the following detailed description and the accompanying drawings.

BRIEF DESCRIPTION OF THE DRAWINGS

FIG. 3 is a cross-sectional view taken along line 3-3 of FIG. 1;

FIG. 5 is a cross-sectional view about the arm;

DETAILED DESCRIPTION OF VARIOUS EMBODIMENTS

The invention will now be further described with reference to the accompanying drawings, which are shown by way of illustration of specific embodiments in which the invention may be practiced. It is to be understood that other embodiments may be utilized and structural and functional changes may be made without departing from the spirit and scope of the present invention.

Figure 1:
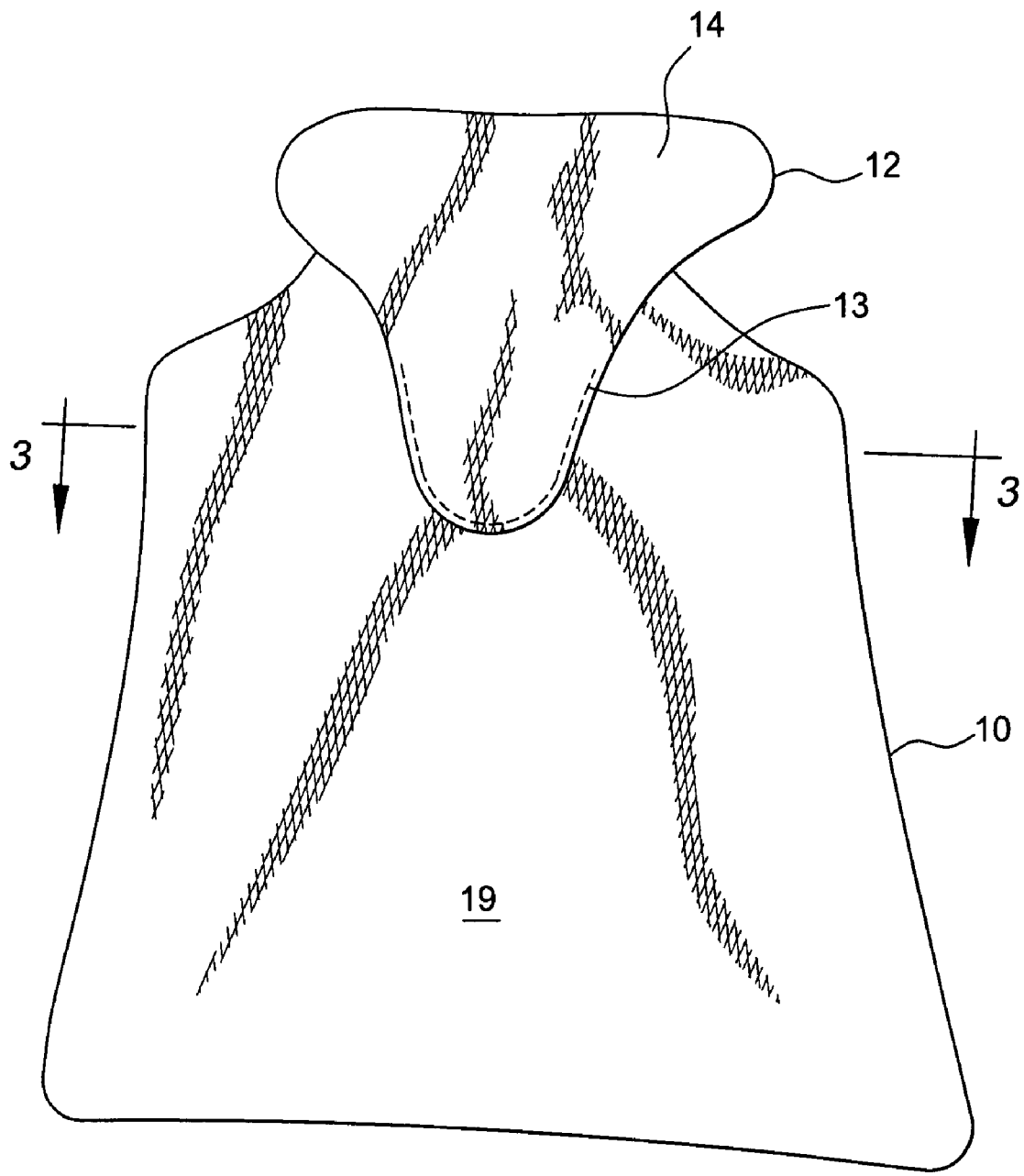
FIG. 1 is a plan view showing one side of a thumb spica assembly illustrating the principles of the invention.
Figure 2:
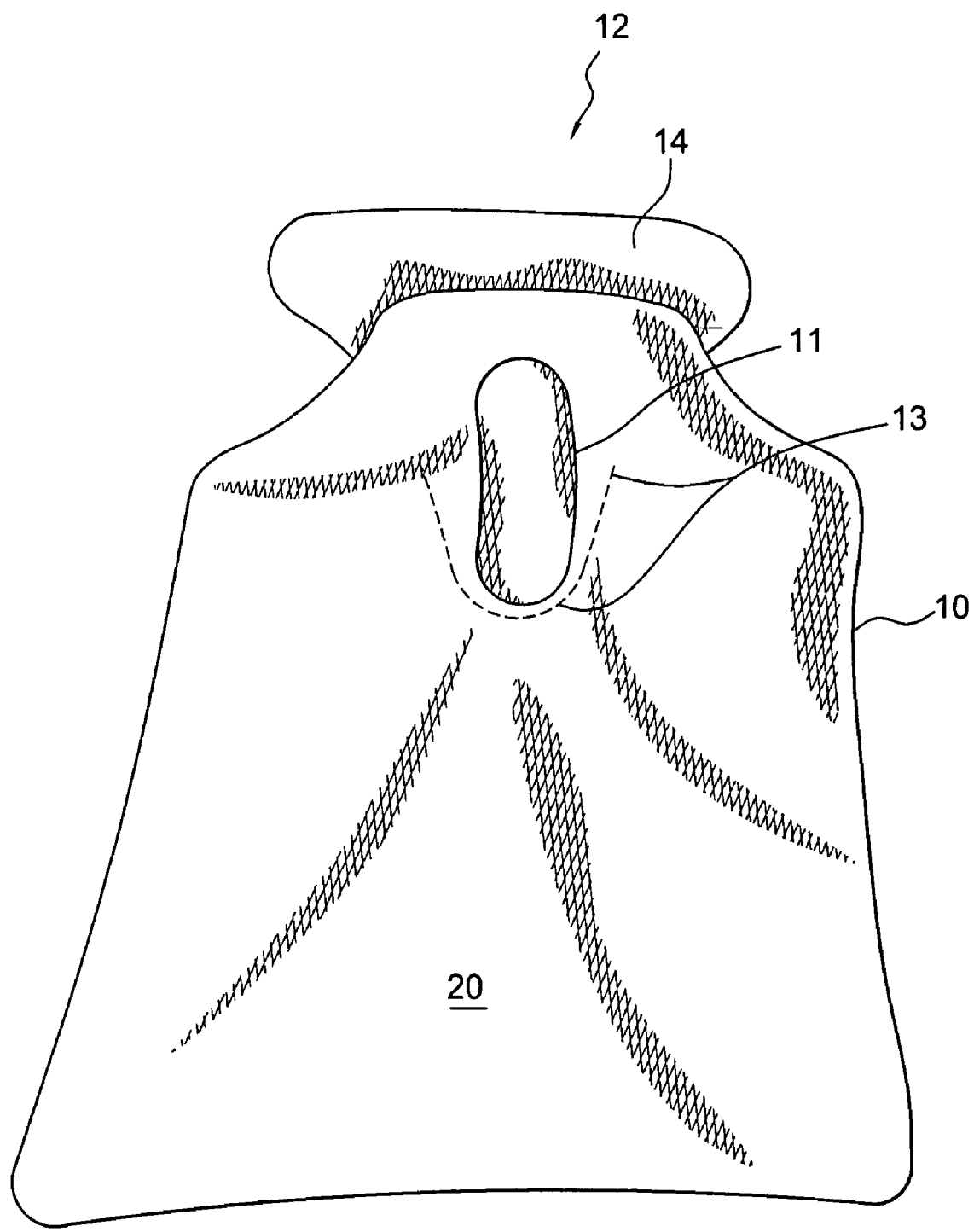
FIG. 2 is the opposite view showing the opposite or inner side of the assembly of FIG. 1.

With reference initially to FIGS. 1-6 of the drawings, a cast for a hand to promote healing of an injury to the hand, wrist, or fingers, may be formed of two materials. There is a first material or blank 10, which is initially flexible and can be formed of a woven or knitted material, impregnated with a water hardenable material such as polyurethane. Once hardened, this material can form a suitably rigid structure to relatively immobilize a portion of the body such as the hand, wrist or arm. As shown in FIG. 2, the material or blank 10 includes an aperture 11 for receiving a thumb 16.

As shown, a second material or outrigger 12, such as a thumb spica, is affixed by stitching or the like 13 around at least a portion of the periphery of the aperture 11 for accommodating the thumb. FIG. 2 shows that the outrigger 12 is secured near and about the periphery of the aperture 11 short of an entire periphery of the aperture 11. The remainders of the material 12, which is shown in the drawing as the top portion 14, extend generally free as a flap relative to the first material or blank 10. The configuration of the outrigger 12 permits it to be individually fit about a thumb (or other corresponding anatomy) relative to the fitting by the blank 10.

The first material or blank 10 and second material or outrigger 12 can be formed of three component elements. A first element or surface 19 provides a net-like surface, a second surface 20 provides another net-like surface, and between them there is a cellular formation 21 which absorbs a hardenable material or can otherwise be treated to become rigid and thereby form the rigid cast around the bodily part to be immobilized. Both net-like surfaces are also able to encompass a hardenable material to add to the rigidity of the cast. The materials 10 and 12 may be formed of double knit-type fabric with an outer woven or knit fabric layers 19 and 20, and an inner woven or knit fabric layer with these two layers being spaced apart and secured together with a matrix 21 of filaments which extend between and which are integrally woven or knit into the outer and inner layers 19 and 20.

The first material 10 and the second material 12 are impregnated with a chemical constituent which is treatable to change from a flexible state to a rigid state. As such, the first and second materials 10 and 12 include at least three layers: a first boundary layer, a second boundary layer, and a cellular layer or matrix of filaments between the first and second boundary layers. The assembly is impregnated with a polyurethane suitable under treatment to cause the first material and second material to form a rigid configuration.

The first material or blank 10 can overlap at its edges 15 and 18, respectively, as shown in FIG. 5 at the intersection 26, and the edges can bond together in this overlapping area. It is in these areas that the benefits of reducing the material profile can be seen.

There can also be additional padding material 22 provided in the form of foam, felt or additional spacer or double knit type material on the inside of the blank 19. This third material 22, may be a gauze-like cotton material, or can be some other cushioning material, suitable to provide padding. In certain situations this material 22 can be of a nature so that it does not absorb moisture caused by perspiration. As such, this material 22 would retain its cushioning effect and not become stiffened or lose its cushioning. A suitable foam-like material, which is breathable, or spacer material, can also be used as material 22. This material retains its flexibility and is not impregnated with water hardenable material.

The third or padding material 22 inside the blank 10 is located adjacent to the bodily portion, including the web between the thumb 16 and the index finger 17. The web includes a peripheral portion which is particularly prone to discomfort, trauma or ulceration when a rigid cast immobilizes the hand, wrist or lower arm, and a rough hardened edge is adjacent the web. The third material, namely the padding material 22, minimizes this discomfort, and in combination with the new outrigger design, essentially eliminates this problem.

In practice, the padding material 22, is initially wrapped around or extended over the forearm, hand and thumb. Then the impregnated parts 10 and 12 of the assembly are dipped into water to start the hardening process. The thumb 16 is then pushed through the aperture 11 by applying the thumb from the side 20 of blank 10 onto the second material 12. The second material 12 is then wrapped around the thumb 16. The second material 12 can either extend completely around the thumb 16 providing circumferential immobilization or the ends can be folded back to only extend part way around the thumb 16 and provide only splinting support. The blank 10 is concurrently wrapped around the forearm, overlying the padding material, and is secured in place by overlapping, by Velcro® material with an elastic ace wrap, or by straps, for specific examples. The forearm, hand and thumb are carefully maintained in the desired orientation for the few minutes required for hardening of the impregnated parts 10 and 12.

The padding material 22, which is adjacent to the periphery of the aperture 11 extends over the area adjacent the periphery of the web and the web portion of the thumb and aperture. This provides for a suitable cushioning of this sensitive area between the thumb and the index finger. This material 22, after the cast is formed rigidly, is under the cast, adjacent to the hand and thumb, and is located in place to provide the cushioning.

Figure 4:
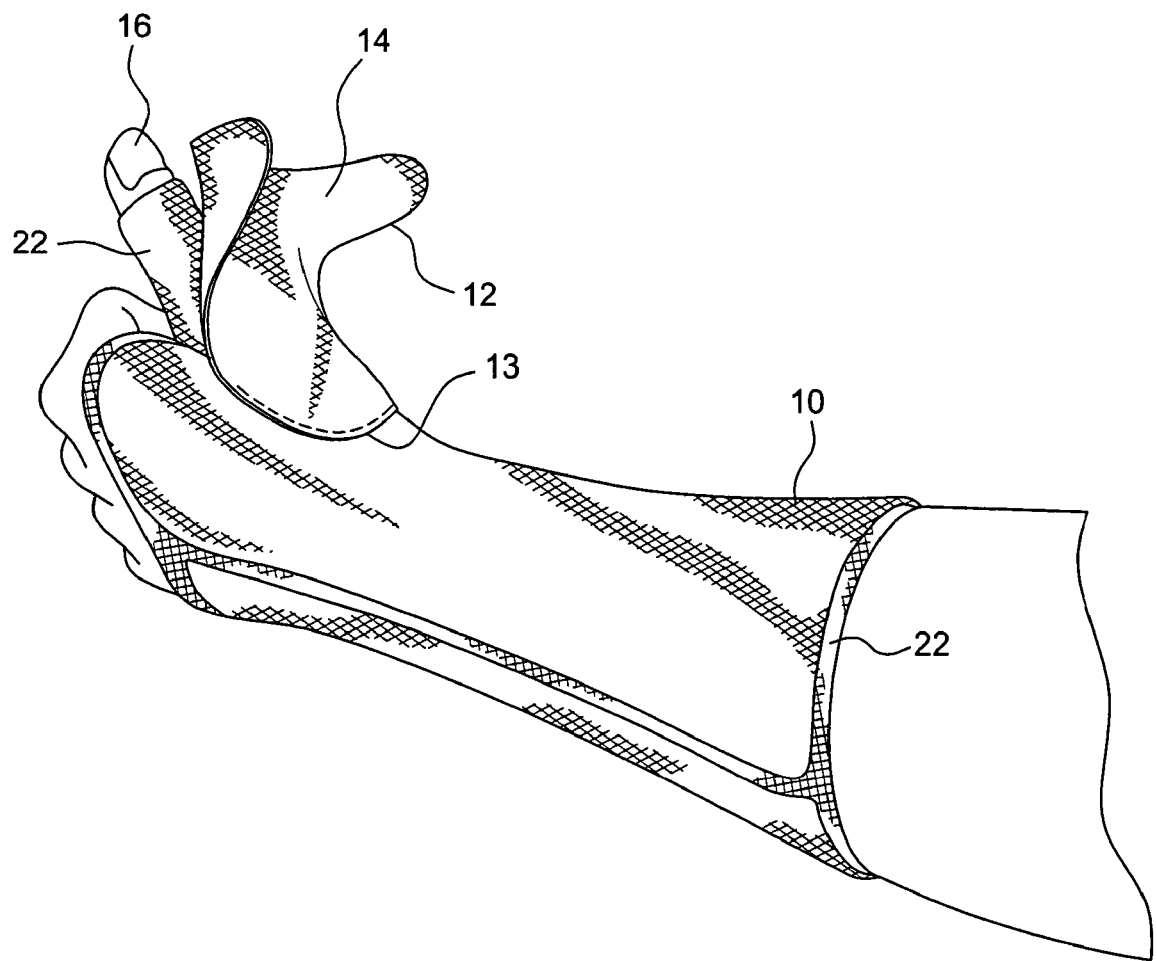
FIG. 4 is a perspective view showing the cast over the lower arm, wrist, and part of the hand and the thumb without a wrapping material.

FIG. 4 shows the cast or support assembly 10, 12 as it is being applied to the forearm, hand and thumb 16. In FIG. 4 the blank 10 has been dipped in water and has been mounted on the forearm with the thumb extending through the oversize thumb hole 11 (see FIG. 2). The thumb spica flap 12 is secured to the blank 10 and is ready to be wrapped around the thumb 16.

Figure 6:
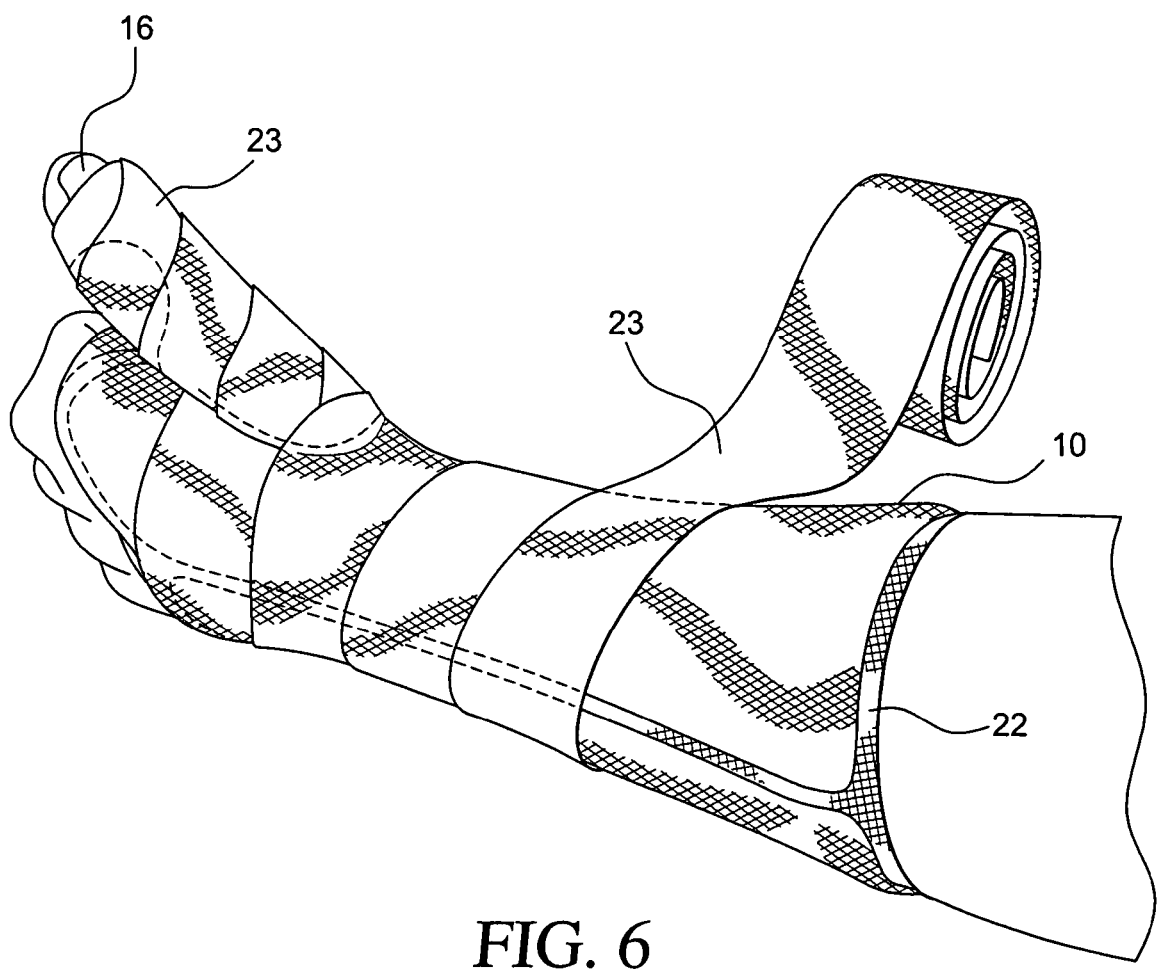
FIG. 6 is a perspective view similar to FIG. 4 with additional tape being applied over the basic cast construction.

Turning now to FIG. 6, a tape 23 is shown in the process of being wrapped around the casting blank 10 and the thumb spica flap 12. The tape 23 may be casting tape, impregnated with water hardening material to bond with the water hardening material of the blank 10 and (optionally) flap 12.

Alternatively, in cases where the injury is less severe, the tape 23 may be a non-impregnated, elastic or stretchable tape such as Ace® bandage tape which is tended to hold the casting blank 10 and outrigger piece 12 in place.

It is further noted that, instead of the additional tape 23, the basic cast or support assembly 10 and outrigger piece 12 may be held in position by bonded overlapping edges as shown in FIG. 5, by mating hook and loop fabric material on the edges of blank 10 and outrigger piece 12 by straps, or by any other desired technique.

By having the second material 12 separate from the first material 10 at least over the greater portion of the periphery of opening 11, or only attached in part to the first material 10, there is achieved a construction which minimizes the irritation around the web area of the hand between the thumb 16 and index finger. This construction also allows for better conformation to the thumb and hand.

Figure 7:
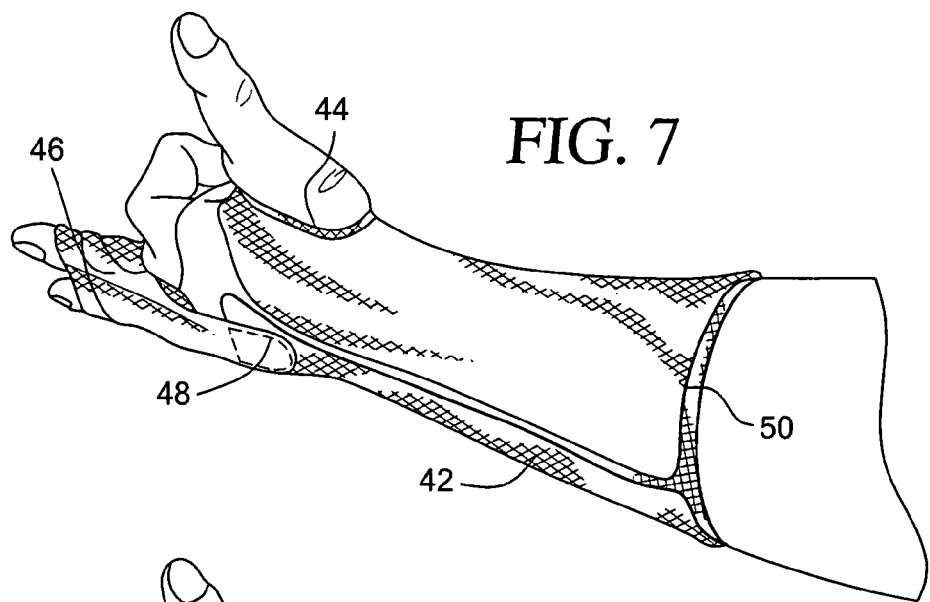
FIG. 7 is a perspective view of another outrigger cast or support construction in which both the undercast padding and the hardenable material have thumb holes.

Referring now to FIG. 7 of the drawings, it shows an ulnar gutter support, including the basic blank 42 with a thumbhole 44, and an outrigger 46 attached to the blank 42 by stitching 48. The outrigger attachment 46 serves to hold or support the two smallest fingers of the hand while recovery from the injury is taking place. The underpadding 50, which is also provided with a thumbhole for positioning and retention, is also shown in FIG. 7.

Figure 8:
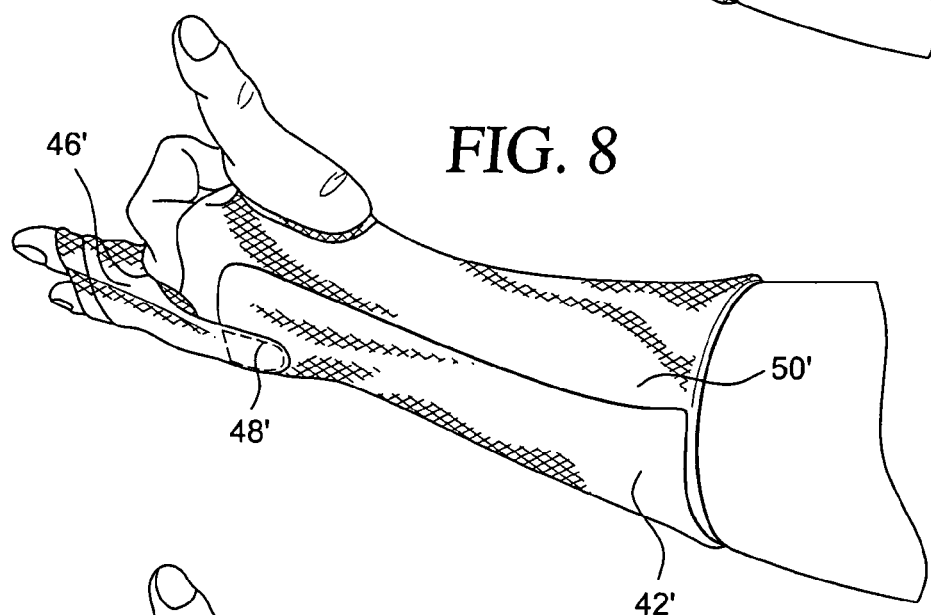
FIG. 8 is a perspective view of a simpler embodiment of an ulnar gutter outrigger support or cast.

The outrigger cast or support of FIG. 8 is similar to that of FIG. 7, and corresponding primed reference numerals are employed. FIG. 8 is similar to that of FIG. 7, in the use of a casting blank 42' which only extends partway around the forearm. It is contemplated that the configuration of FIG. 8 would be for less severe injuries, where less support is needed. In order to hold the hardened support 42, 42' in place, an elasticized tape such as an Ace® bandage of the type shown at reference numeral 23 in FIG. 6 of the drawings may be employed. Other retention arrangements such as straps could also be used.

Figure 9:
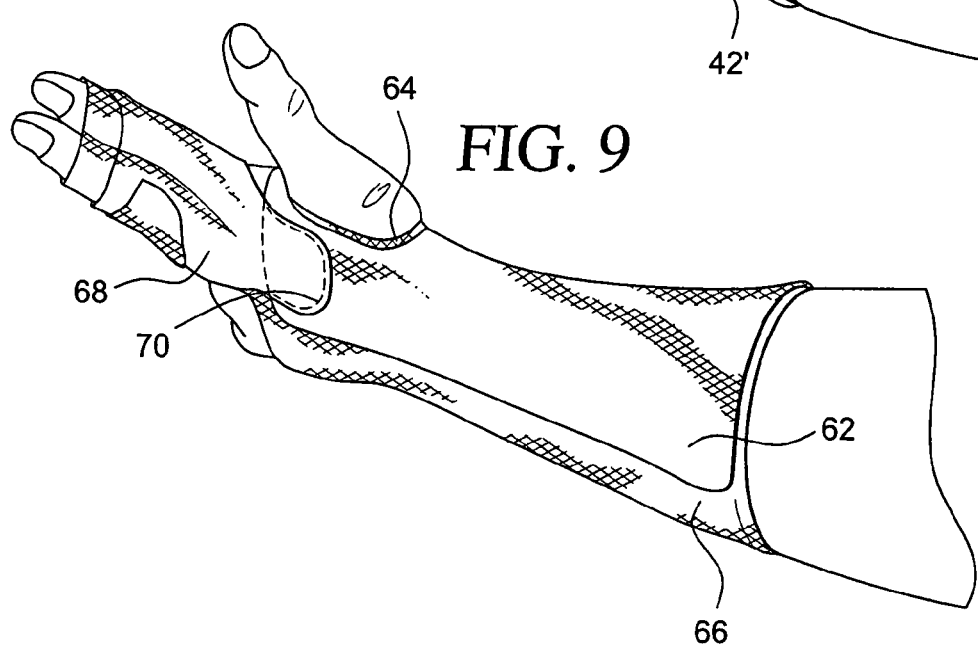
FIG. 9 is a perspective view of a radial gutter cast or support for the index finger and an adjacent finger.

FIG. 9 shows another outrigger embodiment in which a blank 62, impregnated with water hardenable material, and having a thumbhole 64, may be employed. Underlying the support blank 62 is padding material 66. An outrigger flap 68, also impregnated with water hardenable material, is secured to the blank 62 by stitching 70 or other retention arrangements, on both sides of the hand. As in the case of other supports disclosed in this application, the blank 62 may be held in place by tape, either impregnated or elastic, or by straps, or otherwise as disclosed herein. The blank 42, 42', 62 is shown as extending only part way around the forearm, but could be fully circumferential, and may have edges which overlap as disclosed elsewhere herein.

It is noted in passing that the outrigger support configurations as shown in this specification are preferably formed of a separate impregnated flap of impregnated material. However, for some configurations, particularly for an ulnar gutter outrigger, for specific example, the outrigger and forearm support blank could be formed from a single, more elaborately precut or preformed blank having an integral wraparound outrigger portion extending beyond the main portion of the blank on the forearm.

The invention has been described with reference to a cast for immobilizing the hand and providing for cushioning and padding for the web portion between the thumb and the index finger 17. There can be other situations where one of the materials provides cushioning for other sensitive parts of the body members, while a second related material provides relative immobilization to other parts of the body.

Instead of stitching part 13 around the part of the aperture or hole 11, there can be other means to affix the outrigger material 12 to the first material 10. The outrigger is configured for either permanent or removable securing to the first material or blank 10, and may use hook and loop material for securing or direct bonding of the hardening material in the blank and in the finger supporting outrigger. Preferably, an at least partially separate material component is used for forming the cast for the thumb or other fingers. In some cases, the outrigger 12 can be initially totally separate and then joined by the tape 23 or otherwise as mentioned herein to make an integral system.

In the foregoing detailed description and in the drawings, preferred embodiments of the invention have been disclosed. However, various changes and modifications may be made without departing from the spirit and scope of the invention. Thus, by way of example and not of limitation, the padding material may be made of stockinette material, or double knit type material, or of other padding fabric. Similarly, the flaps may be secured in position by stitching, overlapping bonding of hardenable material, by an impregnated tape, by Velcro® type material, by adhesive, or by any other known method. Incidentally, when the word "finger" is used in the present specification and claims, it is understood that the term "finger" includes the thumb. It is further noted that the assemblies of the present invention are packaged in moisture and water vapor impermeable packaging prior to use. Accordingly, the present invention is not limited to the embodiments shown in the drawings and described in detail herein.

The invention claimed is:

1. A cast or support for a hand for use in promoting healing of an injury of the hand comprising:
    a first material initially flexible and being configured for wrapping about the forearm, and being capable of forming a rigid member to limit movement of an injured bodily part; and
    an essentially flat outrigger formed from a second material, at least partially separated from the first material, the outrigger being initially flexible and for location about a thumb or other finger, the outrigger being capable of forming a rigid member to limit movement of the thumb or other finger, and the outrigger being configured for mounting on the first material;
    wherein the outrigger freely extends from the first material so as to individually fit about the thumb or other finger relative to the blank.

2. The cast or support according to claim 1 further comprising flexible padding material for location inside at least the first material for providing a cushioning effect to the bodily part adjacent to the inner surface when it is formed into a rigid format.

3. The cast or support according to claim 2 wherein the padding material is a cotton gauze-like material, and including padding material for location inside the outrigger adjacent to the thumb.

4. The cast or support according to claim 2 wherein the padding material is spacer or double knit type material.

5. The cast or support according to claim 1 wherein the first material has a hole for the thumb to protrude from the one side of the first material to the other side of the first material, and wherein the outrigger essentially covers the hole prior to usage, the outrigger being affixed to the first material and extending beyond the periphery of the hole, and selectively beyond the periphery formed by the first material prior to usage.

6. The cast or support according to claim 5 wherein when a thumb is located in the hole, and the outrigger is wrapped about and caused to embrace the thumb, the edge of the first material around the hole lies adjacent to but does not engage the web between the thumb and forefinger of the patient's hand.

7. The cast or support according to claim 1 wherein the first material and the outrigger are joined prior to being formed into rigid formats.

8. The cast or support according to claim 1 wherein the first material and the outrigger are each a knitted or woven format, and each receives a chemical constituent treatable to change the materials from a flexible state to a rigid state, the first and second materials including at least three layers, the layers being a boundary layer, a cellular layer between the boundary layer and the second boundary layer, the cellular layer being for absorbing the chemical constituent suitable under treatment to cause the first material and second material to form a rigid construction.

9. The cast or support according to claim 1 wherein the first material is in the form of a blank having an irregular configuration to fit the forearm of a patient, and the outrigger is affixed to the first material and extends beyond the periphery formed by the first material prior to usage.

10. The cast or support assembly according to claim 1 wherein the first material defines a hole for receiving a thumb or other finger, the outrigger being secured near and about the edge of the hole short of an entire periphery of the hole.

11. The cast or support according to claim 1 wherein the outrigger is removably attached to the first material.

12. A cast for a bodily part for use in promoting healing of an injury of a bodily part comprising:
    a first material initially flexible and subsequently treatable to form a rigid cast member to limited movement of a first bodily part of injured bodily part;
    a second material initially flexible and subsequently treatable to form a rigid cast member to limit movement of the second bodily part, the second material forming a flap prior to being formed into a rigid format; and
    the first material and the second material being joined prior being formed into rigid formats, and wherein part of the first material is for location adjacent to a web portion of the hand between the thumb and an index finger; and
    the first material defining a hole for the thumb to protrude from one side of the first material to the other side of the first material, and the second material essentially covering the hole prior to usage, the second material being affixed to the first material and extending beyond the periphery of the hole and selectively beyond the periphery formed by the first material prior to usage.

13. The cast according to claim 12 wherein the first and second material are formed of spacer material, the spacer material including inner and outer woven or knit layers spaced apart by an openwork matrix of filaments which are integrally woven or knit into the inner and outer layers.

14. The cast according to claim 12 including tape for holding the cast or support onto the anatomy of the patient.

15. The cast according to claim 12 further including spacer type padding material underlying the blank and the outrigger.

16. The cast according to claim 12 wherein the second material is secured near and about the periphery of the hole short of an entire periphery of the hole.

17. An orthopaedic cast or support including a thumb spica comprising:
    a blank formed of a fabric for application to the forearm of a patient, the fabric being impregnated with water hardenable material, the blank defining a hole for receiving a thumb of a patient;
    an outrigger defined as a flap of fabric secured to the blank along the edge of the hole and freely extending therefrom so as to individually fit about the thumb relative to the blank, the outrigger being dimensioned to fit around the thumb of the patient, and being impregnated with water hardenable material; and the outrigger having a base portion configured for mounting to the blank at a location corresponding to the outer area of the thumb away from the forefinger;

wherein the outrigger is secured near and about the edge of the hole short of an entire periphery of the hole.

18. The cast or support according to claim 17 wherein the blank and the outrigger are both formed from a double knit type material with outer knit or woven layers and an inner matrix of filaments extending between the outer layers and being integrally woven or knit into the layers.

19. The cast or support assembly according to claim 17 wherein the outrigger is removably attached to the blank.

* * * * *